(12) United States Patent
Gonda et al.

(10) Patent No.: US 7,490,603 B2
(45) Date of Patent: *Feb. 17, 2009

(54) METHOD OF USE OF MONOMERIC INSULIN AS A MEANS FOR IMPROVING THE REPRODUCIBILITY OF INHALED INSULIN

(75) Inventors: Igor Gonda, Melbourne (AU); Reid M. Rubsamen, Alamo, CA (US); Stephen J. Farr, Orinda, CA (US)

(73) Assignee: Aradigm Corporation, Hayward, CA (US)

( * ) Notice: Subject to any disclaimer, the term of this patent is extended or adjusted under 35 U.S.C. 154(b) by 422 days.

This patent is subject to a terminal disclaimer.

(21) Appl. No.: 11/284,579

(22) Filed: Nov. 21, 2005

(65) Prior Publication Data

US 2006/0093556 A1 May 4, 2006

Related U.S. Application Data

(60) Continuation of application No. 10/682,529, filed on Oct. 8, 2003, now Pat. No. 7,021,309, which is a continuation of application No. 10/212,897, filed on Aug. 5, 2002, now abandoned, which is a continuation of application No. 09/975,085, filed on Oct. 9, 2001, now Pat. No. 6,431,167, which is a continuation of application No. 09/888,094, filed on Jun. 21, 2001, now Pat. No. 6,427,681, which is a continuation of application No. 09/656,535, filed on Sep. 7, 2000, now Pat. No. 6,250,298, which is a division of application No. 09/004,756, filed on Jan. 8, 1998, now Pat. No. 6,131,567, which is a continuation-in-part of application No. 08/792,616, filed on Jan. 31, 1997, now Pat. No. 5,888,477, which is a continuation-in-part of application No. 08/754,423, filed on Nov. 22, 1996, now Pat. No. 5,743,250, which is a continuation-in-part of application No. 08/549,343, filed on Oct. 27, 1995, now Pat. No. 5,915,378, which is a continuation-in-part of application No. 08/331,056, filed on Oct. 28, 1994, now Pat. No. 5,672,581, which is a continuation-in-part of application No. 08/011,281, filed on Jan. 29, 1993, now Pat. No. 5,364,838.

(51) Int. Cl.
*A61M 11/00* (2006.01)

(52) U.S. Cl. .................. 128/200.14; 128/203.12; 128/204.23

(58) Field of Classification Search ............ 128/200.14, 128/200.23, 203.12, 203.13, 200.22, 200.16, 128/203.15, 203.26, 204.23

See application file for complete search history.

(56) References Cited

U.S. PATENT DOCUMENTS 3,812,854 A * 5/1974 Michaels et al. ....... 128/200.16

(Continued)

FOREIGN PATENT DOCUMENTS

EP 0 186 280 10/1985

(Continued)

OTHER PUBLICATIONS

Barker et al., *J. Exp. Med.*, 168:1493-1498 (1988).

(Continued)

*Primary Examiner*—Danton DeMille
(74) *Attorney, Agent, or Firm*—Karl Bozicevic; Bozicevic, Field & Francis LLP

(57) ABSTRACT

The need for the delivery of insulin by injection can be reduced or eliminated by delivering an aerosolized monomeric insulin formulation. Repeatability of dosing and more particularly the repeatability of the blood concentration versus time profile is improved relative to regular insulin. The blood concentration versus time profile is substantially unaffected by specific aspects of the patient's breathing maneuver at delivery. Further, the rate at which blood glucose is lowered is increased by the use of monomeric insulin. Particles of insulin and in particular monomeric insulin delivered to the surface of lung tissue will be absorbed into the circulatory system. The monomeric insulin may be a dry powder but is preferably in a liquid formulation delivered to the patient from a hand-held, self-contained device which automatically releases an aerosolized burst of formulation. The device includes a sensor which is preferably electronic which measures inspiratory flow and volume which measurement can be used to control the point of drug release.

19 Claims, 3 Drawing Sheets

U.S. PATENT DOCUMENTS

| | | | |
|---|---|---|---|
| 3,991,304 A | 11/1976 | Hillsman | |
| 4,106,503 A | 8/1978 | Rosenthal | |
| 4,343,798 A | 8/1982 | Fawri | |
| 4,361,401 A | 11/1982 | Smith et al. | |
| 4,468,464 A | 8/1984 | Cohen et al. | |
| 4,604,847 A | 8/1986 | Moulding, Jr. et al. | |
| 4,624,251 A | 11/1986 | Miller | |
| 4,627,432 A | 12/1986 | Newell et al. | |
| 4,639,435 A | 1/1987 | Fujii et al. | |
| 4,677,975 A * | 7/1987 | Edgar et al. | 128/200.14 |
| 4,686,231 A | 8/1987 | Bender et al. | |
| 4,727,028 A | 2/1988 | Santerre et al. | |
| 4,755,383 A | 7/1988 | Fujii et al. | |
| 4,819,629 A | 4/1989 | Jonson | |
| 4,877,989 A | 10/1989 | Drews et al. | |
| 4,926,852 A | 5/1990 | Zoltan et al. | |
| 4,984,158 A * | 1/1991 | Hillsman | 128/200.14 |
| 5,006,343 A | 4/1991 | Benson et al. | |
| 5,011,678 A | 4/1991 | Wang et al. | |
| 5,113,855 A * | 5/1992 | Newhouse | 128/203.12 |
| 5,167,506 A | 12/1992 | Kilis et al. | |
| 5,198,541 A | 3/1993 | Elsbach et al. | |
| 5,226,411 A * | 7/1993 | Levine | 128/203.26 |
| 5,284,133 A | 2/1994 | Burns et al. | |
| 5,320,094 A | 6/1994 | Laube et al. | |
| 5,333,106 A | 7/1994 | Lanpher et al. | |
| 5,363,842 A | 11/1994 | Mishelevich et al. | |
| 5,364,838 A | 11/1994 | Rubsamen | |
| 5,394,866 A | 3/1995 | Ritson et al. | |
| 5,404,871 A | 4/1995 | Goodman et al. | |
| 5,437,267 A | 8/1995 | Weinstein et al. | |
| 5,446,020 A | 8/1995 | Andy et al. | |
| 5,450,336 A | 9/1995 | Rubsamen et al. | |
| 5,497,944 A | 3/1996 | Weston et al. | |
| 5,509,404 A | 4/1996 | Lloyd et al. | |
| 5,514,646 A | 5/1996 | Chance et al. | |
| 5,522,385 A | 6/1996 | Lloyd et al. | |
| 5,529,055 A | 6/1996 | Gueret | |
| 5,544,646 A | 8/1996 | Lloyd et al. | |
| 5,547,929 A | 8/1996 | Anderson | |
| 5,693,608 A | 12/1997 | Bechgaard et al. | |
| 5,694,920 A | 12/1997 | Abrams et al. | |
| 5,700,662 A | 12/1997 | Chance et al. | |
| 5,743,250 A | 4/1998 | Gonda et al. | |
| 6,131,567 A * | 10/2000 | Gonda et al. | 128/200.14 |

FOREIGN PATENT DOCUMENTS

| | | | |
|---|---|---|---|
| EP | 0 200 383 | | 12/1986 |
| EP | 0 233 235 A2 | | 8/1987 |
| EP | 0 272 489 | | 6/1988 |
| FR | 2673142 | | 8/1992 |
| GB | 2 153 081 A | | 8/1985 |
| GB | 2164569 A | * | 3/1986 |
| GB | 2 255 918 | | 11/1992 |
| GB | 2 256 805 | | 12/1992 |
| GB | 2 104 393 | | 3/1993 |
| JP | H03-99667 A | | 4/1991 |
| JP | H04-100557 A | | 4/1992 |
| JP | H05-31421 A | | 2/1993 |
| JP | H05-123399 A | | 5/1993 |
| WO | US 88/02700 | | 8/1988 |
| WO | WO 89/01486 | | 2/1989 |
| WO | US 90/00837 | | 2/1990 |
| WO | WO 90/12814 | | 11/1990 |
| WO | WO 91/14468 | | 10/1991 |
| WO | WO 92/03535 | | 3/1992 |
| WO | GB 91/01868 | | 5/1992 |
| WO | WO 92/07599 | | 5/1992 |
| WO | WO 92/09322 | | 6/1992 |
| WO | US 92/01815 | | 9/1992 |
| WO | WO 92/15353 | | 9/1992 |
| WO | WO 93/17728 | | 9/1993 |
| WO | WO 96/00046 | | 1/1996 |
| WO | WO 96/09846 | | 4/1996 |
| WO | WO 96/13290 | | 5/1996 |

OTHER PUBLICATIONS

Berger et al., *Methods in Enzymology*, 152:664-704 (1987).
Collins et al., *Nature*, 270:347-349 (1977).
Colthorpe et al., *Pharmaceutical Research*, 9:764-8 (1992).
Drazin et al., *Infect. Immun.*, 382-388 (1977).
Elliott et al., *Aust. Paediatr. J.*, 23:293-297 (1987).
Elsbach et al., *The Journal of Biological Chemistry*, 254:11000-11009 (1979).
Elsbach et al., *Bacyeria-Host Cell Interaction*, 47-60 (1988).
Farley et al., *Infection and Immunology*, 55:1536-1539 (1987).
Gabay et al., *Proc. Natl. Acad. Sci. USA*, 86:5610-5614 (1989).
Gabay et al., *Clinical Research*, 34:676A (1986).
Gabay et al., *J. Exp. Med.*, 186:1407-1421 (1986).
Ganz et al., *J. Clin. Invest.*, 76:1427-1435 (1985).
Gray et al., *The Journal of Biological Chemistry*, 264:9505-9509 (1989).
Gray et al., *Clinical Research*, 36:620A (1988).
Gubler et al., *Gene*, 25:264-269 (1983).
Heck et al., *Anal. Biochem.*, 149:153-162 (1985).
Heck et al., *Anal. Biochem.*, 158:217-227 (1986).
Heron, *Am. Biotechnol. Lab.*, 2:52-54, 56, 58-59 (1984).
Hovde et al., *Infect. Immun.*, 52:90-95 (1986).
Hovde et al., *Infection and Immunity*, 54:142-148 (1986).
Hunkapiller et al., *Meth. Enzymol.*, 91:399-413 (1983).
Klein, *Immunology: The Science of Self-Nonself Discrimination*, John Wiley & Sons, NY p. 101.
Kohler, D., *Lung, Suppl.* 677-84 (1990).
Larrick et al., *Biochem. Biophys. Research Communications*, 179:170-175 (1991).
Laube et al., *Journal Aerosol Medicine*, 4:286 (1991).
Laube et al., *JAMA*, 269:2106-2109 (1994).
Lehrer et al., *Infect. Immun.*, 49:207-211 (1985).
Maniatis et al., (eds.) *Molecular Cloning: A Laboratory Manual.* Cold Spring Harbor Laboratory, Cold Spring Harbor, NY pp. 188-199 (1982).
Moses et al., *Diabetes*, 32:1040-7 (1983).
Muello et al., *Clinical Research*, 31L371A (1983).
Nachman et al., *J. Cell Biol.*, 54:133-140 (1972).
Newman et al., *Thorax*, 36:52-55 (1981).
Newman et al., *Eur. J. Respir. Dis.*, 62:3-21 (1981).
Newman et al. *Am. Rev. Respir. Dis.*, 124:317-320 (1981).
Newman et al., *Deposition and Effects of Inhalation Aerosols*, Royal Free Hospital, London (1983) ISBN-91-86058-03-07.
Odeberg et al., *Infect. Immun.*, 14:1269-1275 (1976).
Odeberg et al., *J. Clin. Invest.*, 56:1118-1124 (1975).
Okayama et al., *Molec. Cell Biol.*, 3:280-289 (1983).
Olsson et al., *Blood*, 44:235-246 (1974).
Ooi et al., *The Journal of Biological Chemistry*, 262:14891-14894 (1987).
Ooi et al., *J. Exp. Med.*, 174:649-655 (1991).
Pereira et al., *Blood*, 76:825-834 (1990).
Remington's Pharmaceutical Sciences, A.R. Gennaro, ed., 1985, Mack Publishing Co.
Rest et al., *Infect. Immun.*, 19:131-137 (1978).
Salvesen et al., *Biochem.* 26:2289-2293 (1987).
Salzman, R., *New England Journal of Medicine*, 213:1078-84 (1985).
Sciarra et al., *Journal of Pharmaceutical Sciences*, 65(4):1519-1522.

Selsted et al., *J. Clin. Invest.*, 76:1436-1439 (1985).
Selsted et al., *J. Biol. Chem.*, 260:4579-4582 (1985).
Selsted et al., *Infect. Immun.*, 49:202-206 (1985).
Selsted et al., *Infect. Immun.*, 45:150-154 (1984).
Shafer et al., *Infection and Immunity*, 45:29-35 (1987).
Spintznagel et al., *The Journal of Immunology*, 139:1291-1296 (1987).
Starkey et al., *Biochem. J.*, 155:255-263 (1976).
Suggs et al., *Proc. Natl. Acad. Sci. USA*, 78:6613-6617 (1981).
Wallace et al., *Nuc. Acids Res.* 9:879-894 (1981).
Weiss et al., *Infection and Immunity*, 38:1149-1153 (1982).
Weiss et al., *The Journal of Immunology*, 132:3109-3115 (1984).
Weiss et al., *The Journal of Biological Chemistry*, 253:3109-3115 (1984).
Weiss et al., *Clinical Research*, 34:537A (1986).
Weiss et al., *Blood*, 69:652-659 (1987).
Weiss et al., *Clinical Research* 33:567A (1985).
Weiss et al., *infection and Immunity*, 51:594-599 (1986).
Weiss et al., *The Journal of Clinical Investigation*, 71:540-549 (1983).
Weiss et al., *Journal of Clinical Investigation*, 71:540-549 (1983).
Wilde et al., *J. Biol. Chem.*, 11200-11203 (1989).
Wigley et al., *Diabetes*, 20:552-556 (1971).
Yoshida et al., *Journal Pharmaceutical Sciences* 68:670-1 (1979).
Young et al., *Proc. Natl. Acad. Sci.*, USA, 80:1194-1198 (1983).

* cited by examiner

METHOD OF USE OF MONOMERIC INSULIN AS A MEANS FOR IMPROVING THE REPRODUCIBILITY OF INHALED INSULIN

CROSS-REFERENCES

This application is a continuation of U.S. application Ser. No. 10/682,529 filed Oct. 8, 2003 which is a continuation of U.S. application Ser. No. 10/212,897, filed Aug. 5, 2002 (now abandoned) which is a continuation of U.S. application Ser. No. 09/975,085, filed Oct. 9, 2001 (now issued U.S. Pat. No. 6,431,167, issued Aug. 13, 2002), which is a continuation of U.S. application Ser. No. 09/888,094, filed Jun. 21, 2001 (now issued U.S. Pat. No. 6,427,681, issued Aug. 6, 2002), which is a continuation of U.S. application Ser. No. 09/656,535 filed Sep. 7, 2000 (now U.S. Pat. No. 6,250,298 issued Jun. 26, 2001) which is a divisional of U.S. application Ser. No. 09/004,756 filed Jan. 8, 1998 (now U.S. Pat. No. 6,131,567 issued Oct. 17, 2000), which is a continuation-in-part of U.S. application Ser. No. 08/792,616 filed Jan. 31, 1997 (now U.S. Pat. No. 5,888,477 issued Mar. 30, 1999) which is a continuation-in-part of application Ser. No. 08/754,423, filed Nov. 22, 1996 (now U.S. Pat. No. 5,743,250 issued Apr. 28, 1998), which is a continuation-in-part of application Ser. No. 08/549,343, filed Oct. 27, 1995 (now issued U.S. Pat. No. 5,915,378, issued Jun. 29, 1999), which is a continuation-in-part of application Ser. No. 08/331,056, filed Oct. 28, 1994 (now U.S. Pat. No. 5,672,581 issued Sep. 30, 1997), which is a continuation-in-part of application Ser. No. 08/011,281, filed Jan. 29, 1993 (now U.S. Pat. No. 5,364,838 issued Nov. 15, 1994) all of which are incorporated herein by reference and to which application we claim priority under 35 U.S.C.§120.

FIELD OF THE INVENTION

This invention relates generally to a method of aerosolized drug delivery. More specifically, this invention relates to the controlled intrapulmonary delivery of a monomeric insulin alone or in combination with other treatment methodologies which are combined to significantly reduce or eliminate the need for administering insulin by injection.

BACKGROUND OF THE INVENTION

Diabetes Mellitus is a disease affecting approximately 7.5 million people in the United States. The underlying cause of this disease is diminished or absent insulin production by the Islets of Langerhans in the pancreas. Of the 7.5 million diagnosed diabetics in the United States, approximately one-third are treated using insulin replacement therapy. Those patients receiving insulin typically self-administer one or more doses of the drug per day by subcutaneous injection. Insulin is a polypeptide with a nominal molecular weight of 6,000 Daltons. Insulin has traditionally been produced by processing pig and cow pancreas to allow isolation of the natural product. More recently, recombinant technology has made it possible to produce human insulin in vitro. It is the currently common practice in the United States to institute the use of recombinant human insulin in all of those patients beginning insulin therapy.

It is known that most proteins are rapidly degraded in the acidic environment of the GI tract. Since insulin is a protein which is readily degraded in the GI tract, those in need of the administration of insulin administer the drug by subcutaneous injection (SC). No satisfactory method of orally administering insulin has been developed. The lack of such an oral delivery formulation for insulin creates a problem in that the administration of drugs by injection can be both psychologically and physically painful.

In an effort to provide for a non-invasive means for administering insulin, and thereby eliminate the need for hypodermic syringes, aerosolized insulin formulations have been tested. Aerosolized insulin formulations have been shown to produce insulin blood levels in man when these aerosols are introduced onto nasal or pulmonary membrane. Moses et al. [*Diabetes,* Vol. 32, November 1983] demonstrated that a hypoglycemic response could be produced following nasal administration of 0.5 units/kg. Significant inter-subject variability was noted, and the nasal insulin formulation included unconjugated bile salts to promote nasal membrane penetration of the drug. Salzman et al. [*New England Journal of Medicine,* Vol. 312, No. 17] demonstrated that an intranasal aerosolized insulin formulation containing a non-ionic detergent membrane penetration enhancer was effective in producing a hypoglycemic response in diabetic volunteers. Their work demonstrated that nasal irritation was present in varying degrees among the patients studied. In that diabetes is a chronic disease which must be continuously treated by the administration of insulin and in that mucosal irritation tends to increase with repeated exposures to the membrane penetration enhancers, efforts at developing a non-invasive means of administering insulin via nasal administration have not been commercialized.

In 1971, Wigley et al. [*Diabetes,* Vol. 20, No. 8] demonstrated that a hypoglycemic response could be observed in patients inhaling an aqueous formulation of insulin into the lung. Radio-immuno assay techniques demonstrated that approximately 10 percent of the inhaled insulin was recovered in the blood of the subjects. Because the surface area of membranes available to absorb insulin is much greater in the lung than in the nose, no membrane penetration enhancers are required for delivery of insulin to the lungs by inhalation. The inefficiency of delivery seen by Wigley was greatly improved in 1979 by Yoshida et al. [*Journal of Pharmaceutical Sciences,* Vol. 68, No. 5] who showed that almost 40 percent of insulin delivered directly into the trachea of rabbits was absorbed into the bloodstream via the respiratory tract. Both Wigley and Yoshida showed that insulin delivered by inhalation could be seen in the bloodstream for two or more hours following inhalation.

Aerosolized insulin therefore can be effectively given if the aerosol is appropriately delivered into the lung. In a review article, Dieter Kohler [*Lung,* supplement pp. 677B684] remarked in 1990 that multiple studies have shown that aerosolized insulin can be delivered into and absorbed from the lung with an expected absorption half-life of 15-25 minutes. However, he comments that "the poor reproducibility of the inhaled dose [of insulin] was always the reason for terminating these experiments." This is an important point in that the lack of precise reproducibility with respect to the administration of insulin is critical. The problems associated with the inefficient administration of insulin cannot be compensated for by administering excess amounts of the drug in that the accidental administration of too much insulin could be fatal.

Effective use of an appropriate nebulizer can achieve high efficiency in delivering insulin to human subjects. Laube et al. [*Journal of Aerosol Medicine,* Vol. 4, No. 3, 1991] have shown that aerosolized insulin delivered from a jet nebulizer with a mass median aerodynamic diameter of 1.12 microns, inhaled via a holding chamber at a slow inspiratory flow rate of 17 liters/minute, produced an effective hypoglycemic response in test subjects at a dose of 0.2 units/kg. Colthorpe et al. [*Pharmaceutical Research,* Vol. 9, No. 6, 1992] have shown that aerosolized insulin given peripherally into the lung of rabbits produces a blood concentration versus time profile of over 50 percent in contrast to 5.6 percent blood concentration versus time profile seen for liquid insulin dripped onto the central airways. Colthorpe's work supports the contention that aerosolized insulin must be delivered peripherally into the lung for maximum efficiency and that inadvertent central deposition of inhaled aerosolized insulin will produce an effect ten times lower than that desired. Variations in dosing of 10-fold are clearly unacceptable with respect to the administration of most drugs, and in particular, with respect to the administration of insulin.

The present invention endeavors to provide a non-invasive methodology for enhancing treatment of diabetic patients via aerosolized delivery.

SUMMARY OF THE INVENTION

Aerosolized delivery of insulin is disclosed wherein the insulin is monomeric insulin. Aerosolized delivery of monomeric insulin is significantly less affected by an inhaling patient's breathing pattern as compared to the effect on conventional recombinant insulin. More specifically, the maximum insulin concentration ($C_{MAX}$) and the time needed to obtain the maximum concentration ($T_{MAX}$) is much less affected by the amount of air inhaled after delivery of aerosolized drug. Accordingly, a higher degree of repeatability of dosing can be obtained (with monomeric insulin as compared to regular insulin) making it substantially more practical for patients to control glucose levels by inhaling insulin-thereby making diabetics less dependent on injecting insulin.

When delivering aerosolized insulin the patient can be coached (by teaching and/or by the device which measures flow rate and/or volume) to inhale at a given rate and to inhale a given amount of air (before and after the aerosol is released). One of the findings disclosed here is that the inhaled volume at delivery does not substantially affect the blood concentration versus time profile for the aerosolized delivery of monomeric insulin. However, the inhaled volume at delivery does substantially affect the blood concentration versus time profile of regular insulin. Accordingly, one aspect of the invention is the aerosolized delivery of monomeric insulin without regard to respiratory maneuver parameters such as inhaled volume. A second aspect of the invention is aerosolized delivery of insulin which is not monomeric insulin while measuring inhaled volume and insuring that the inhaled volume is (1) repeated for each dose in the same amount and (2) preferably a large inhaled volume, e.g. 80% or more of the lung capacity of the patient. It should be noted that to obtain the most repeatable results that monomeric insulin should be delivered each time at substantially the same inspiratory flow rate and inspiratory volume at delivery and such delivery should be followed by the same inhaled volume which is preferably a maximum inhaled volume.

The monomeric insulin formulation may be in any form, e.g., a dry powder, or dispersed or dissolved in a low boiling point propellant. However, the formulation is more preferably an aqueous solution having a pH close to 7.4±1.0 which can be aerosolized into particles having a particle diameter in the range of about 1.0 to about 4.0 microns. Formulations of monomeric insulin are preferably aerosolized and administered via hand-held, self-contained devices which are automatically actuated at the same release point in a patient's inspiratory flow cycle. The release point is automatically determined either mechanically or, more preferably calculated by a microprocessor which receives data from a sensor making it possible to determine inspiratory flow rate and inspiratory volume. The device can measure parameters including inspiratory flow rates and volumes and provide information to the patient which can aid in controlling the patient's respiratory maneuvers. Preferably the device is loaded with a cassette comprised of an outer housing which holds a package of individual disposable collapsible containers of a monomeric insulin analog containing formulation for systemic delivery. Actuation of the device forces the monomeric insulin formulation through a porous membrane of the container which membrane has pores having a diameter in the range of about 0.25 to 3.0 microns, preferably 0.25 to 1.5 microns. The porous membrane is positioned in alignment with a surface of a channel through which a patient inhales air.

The dose of insulin analog to be delivered to the patient varies with a number of factors—most importantly the patient's blood glucose level. Thus, the device can deliver all or any proportional amount of the formulation present in the container. If only part of the contents are aerosolized the remainder may be discarded. By delivering any proportional amount of a container the patient can adjust the dose to any desired level while using containers which all contain the same amount of monomeric insulin.

Smaller particle sizes are preferred to obtain systemic delivery of insulin analog. Thus, in one embodiment, after the aerosolized mist is released into the channel the air surrounding the particles may be heated in an amount sufficient to evaporate carrier and thereby reduce particle size. The air drawn into the device can be actively heated by moving the air through a heating element which element is pre-heated prior to the beginning of a patient's inhalation. The amount of energy added can be adjusted depending on factors such as the desired particle size, the amount of the carrier to be evaporated, the water vapor content of the surrounding air and the composition of the carrier (see U.S. Pat. No. 5,522,385 issued Jun. 4, 1996).

To obtain systemic delivery it is desirable to get the aerosolized formulation deeply into the lung. This is obtained, in part, by adjusting particle sizes. Particle diameter size is generally about one to three times the diameter of the pore from which the particle is extruded. In that it is technically difficult to make pores of 1.0 microns or less in diameter the use of evaporation can reduce particle size to 3.0 microns or less even with pore sizes well above 1 micron. Energy may be added in an amount sufficient to evaporate all or substantially all carrier and thereby provide particles of dry powdered insulin or highly concentrated insulin formulation to a patient which particles are uniform in size regardless of the surrounding humidity and smaller due to the evaporation of the carrier.

In addition to adjusting particle size, systemic delivery of insulin is obtained by releasing an aerosolized dose at a desired point in a patient's respiratory cycle. When providing systemic delivery it is important that the delivery be reproducible.

Reproducible dosing of insulin to the patient is obtained by: (1) using monomeric insulin which has been shown here to be less affected by the patient's respiratory pattern, and/or; (2) providing for automatic release of formulation in response to a determined inspiratory flow rate and measured inspiratory volume. The automatic release method involves measuring for, determining and/or calculating a firing point or drug release decision based on instantaneously (or real time) calculated, measured and/or determined inspiratory flow rate and inspiratory volume points. To obtain repeatability in dosing, the formulation is repeatedly released at the same measured (1) inspiratory flow rate and (2) inspiratory volume. To maximize the efficiency of delivery aerosols are released at (3) a measured inspiratory flow rate in the range of from about 0.1 to about 2.0 liters/second and (2) a measured inspiratory volume in the range of about 0.1 to about 1.5 liters. After the aerosol is released the patient preferably continues inhaling to a maximum inhalation point.

A primary object of the invention is to provide for a method of increasing the repeatability at which glucose levels can be controlled by aerosol delivery of monomeric insulin.

An advantage of the invention is that the aerosolized delivery of monomeric insulin is substantially less affected by a patient's breathing maneuvers during delivery as compared to regular insulin and specifically is less affected by how much the patient inhales after aerosolized delivery.

A feature of the invention is the commercially available insulin lispro can be used in the method.

Another object is to provide a method of administering a monomeric insulin analog formulation to a patient wherein the formulation is repeatedly delivered to a patient at the same measured inspiratory flow rate (in the range of 0.1 to 2.0 liters/second) and separately determined inspiratory volume (beginning delivery in the range of 0.15 to 1.5 liters and continuing inspiration to maximum, e.g., 4-5 liters).

Another object of the invention is to combine delivery therapies for inhaling monomeric insulin with monitoring technologies so as to maintain tight control over the serum glucose level of a patient suffering from diabetes mellitus.

Another object of the invention is to provide a device which allows for the intrapulmonary delivery of controlled amounts of monomeric insulin formulation based on the particular needs of the diabetic patient including serum glucose levels and insulin sensitivity.

Another object of the invention is to provide a means for treating diabetes mellitus which involves supplementing monomeric insulin administration using an intrapulmonary delivery means in combination with injections of insulin and/or oral hypoglycemic agents such as sulfonylureas.

Another advantage of the present invention is that the methodology allows the administration of a range of different size doses of monomeric insulin by a convenient and painless route, thus decreasing the probability of insulin overdosing and increasing the probability of safely maintaining desired serum glucose levels.

Another feature of the device of the present invention is that it may be programmed to provide variable dosing (from the same size container) so that different doses are delivered to the patient at different times of the day coordinated with meals and/or other factors important to maintain proper serum glucose levels with the particular patient.

Another feature of the invention is that the portable, handheld inhalation device of the invention can be used in combination with a portable device for measuring serum glucose levels in order to closely monitor and titrate dosing based on actual glucose levels.

Yet another feature of the invention is that the microprocessor of the delivery device can be programmed to prevent overdosing by preventing formulation release more than a given number of times within a given period of time.

Another object of the invention is to adjust particle size by heating air surrounding the particles in an amount sufficient to evaporate carrier and reduce total particle size.

Another object is to provide a drug delivery device which includes a desiccator for drying air in a manner so as to remove water vapor and thereby provide consistent particle sizes even when the surrounding humidity varies.

Another object is to provide a device for the delivery of aerosols which measures humidity via a solid state hygrometer.

A feature of the invention is that drug can be dispersed or dissolved in a liquid carrier such as water and dispersed to a patient as dry or substantially dry particles of monomeric insulin.

Another advantage is that the size of the particles delivered will be relatively independent of the surrounding humidity.

It is an object of this invention to demonstrate a novel application for Humalog™ as a monomeric insulin analog well suited for pulmonary drug delivery.

It is an object of this invention to demonstrate that aerosolized delivery of Humalog™ in place of conventional formulations of recombinant human insulin makes a repeatable blood concentration versus time profile substantially less dependent on the patients final inhaled volume at delivery.

It is an object of this invention to demonstrate that aerosolized delivery of Humalog™ in place of conventional formulations of recombinant human insulin makes a repeatable blood concentration versus time profile substantially less dependent of the patients final inhaled volume at delivery.

It is an object of this invention to demonstrate that by increasing the blood concentration versus time profile of the delivered monomeric insulin such as Humalog™ (regardless of breathing maneuver after delivery) that a more reproducible and consistent effect on serum blood glucose can be achieved.

It is another object of this invention to demonstrate that the increased reproducibility seen after the delivery of Humalog™ via aerosolization into the lung results in a more economical approach to the pulmonary drug delivery of insulin than offered by the delivery of regular recombinant human insulin to the lung via aerosolization.

These and other objects, advantages and features of the present invention will become apparent to those persons skilled in the art upon reading the details of the structure of the device, formulation of compositions and methods of use, as more fully set forth below.

DETAILED DESCRIPTION OF PREFERRED EMBODIMENTS

Figure 1:
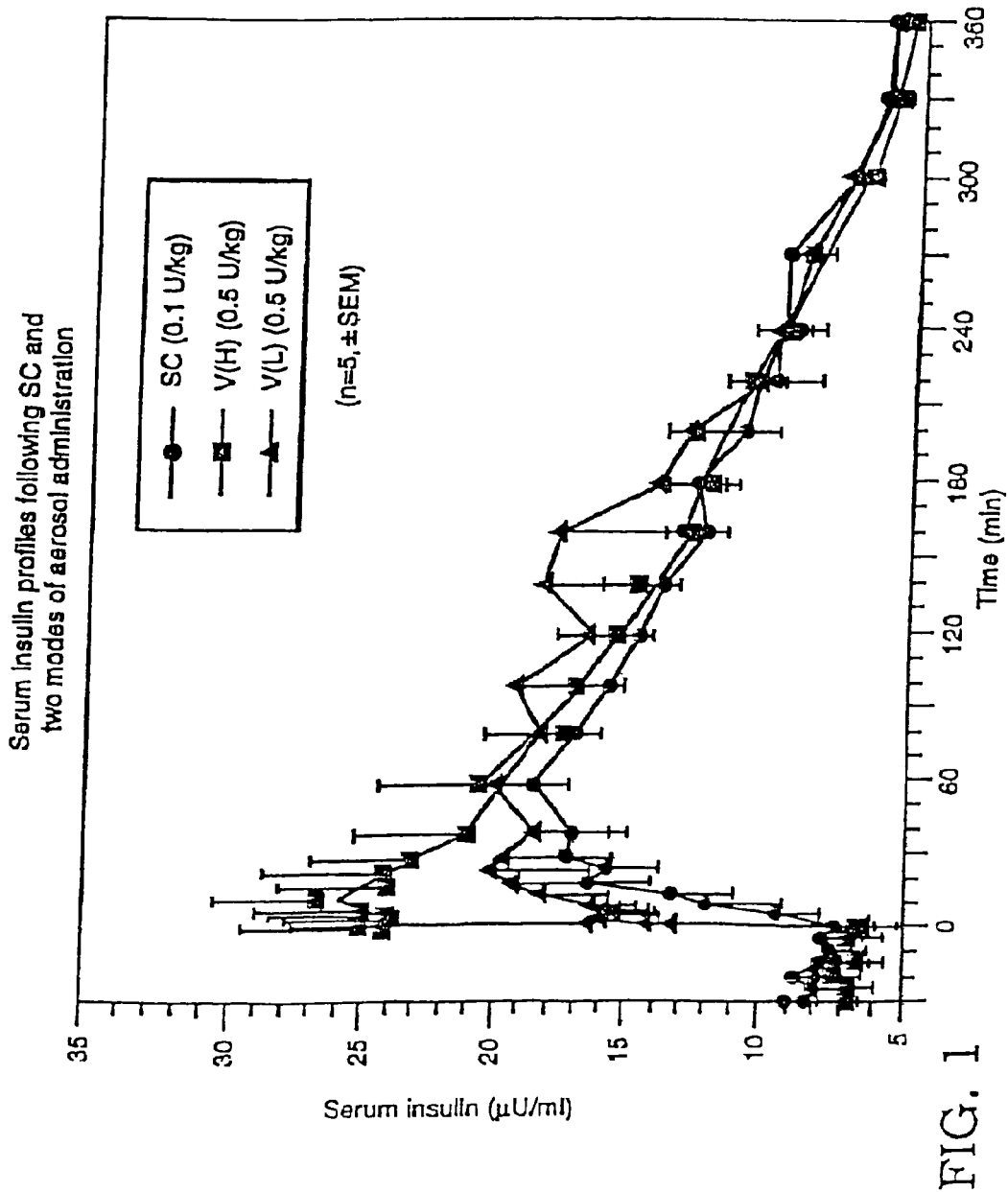
FIG. 1 is a graph plotting the change in serum insulin levels over time following different methods of insulin administration.

Before the present method of delivering aerosolized monomeric insulin to treat diabetes mellitus and devices, containers and formulations used in the treatment are described, it is to be understood that this invention is not limited to the particular methodology, containers, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a formulation" includes mixtures of different formulations, reference to "an analog" refers to one or mixtures of insulin analogs, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods, devices and materials similar or equivalent to those described herein can be used in the practice or testing of the invention, the preferred methods, devices and materials are now described. All publications mentioned herein are incorporated herein by reference for the purpose of describing and disclosing devices, formulations and methodologies which are described in the publication and which might be used in connection with the presently described invention.

Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

Definitions

The term "insulin" shall be interpreted to encompass fast acting "regular" insulin, natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form which includes additional excipients. Regular insulin is preferably recombinantly produced and may be dehydrated (completely dried) or in solution. For purposes of the present invention insulin is particularly characterized by molecules which form complexes, particularly hexamers in solution and when in the human body the hexamer complexes disassociate much more slowly than monomeric insulin.

The "monomeric insulin" is intended to encompass any form of an insulin molecule which is different from regular insulin wherein the difference results in the insulin molecules not maintaining hexamer complexes in a human which hexamers are characteristic of insulin. Monomeric insulin exists predominantly in a monomer form or quickly dissociates into a monomeric form in the human body. The change which induces the monomeric form may be caused by one or more of the amino acids within the polypeptide chain being replaced with an alternative amino acid and/or wherein one or more of the amino acids has been deleted or wherein one or more additional amino acids has been added to the polypeptide chain or amino acid sequences which act as insulin in decreasing blood glucose levels and/or where bonds such as disulfide bonds are deleted, added or moved in position relative to natural human insulin. The change may also by obtained by using a different salt form e.g. replacing the zinc cations with sodium cations. The preferred monomeric insulin is insulin lispro in a zinc salt form as disclosed in U.S. Pat. No. 5,547,929, issued Aug. 20, 1996 and see also U.S. Pat. Nos. 5,514,646 and 5,700,662 all of which are incorporated herein by reference. It should be noted that insulin as well as monomeric insulin will disassociate into monomeric forms over time. However, monomeric insulin will disassociate into the monomeric form, in a human body, at twice the rate or faster than insulin when it is administered subcutaneously. It should be noted that insulin lispro disassociates into the monomeric form at approximately three times the rate as compared to regular insulin when it is administered subcutaneously.

The terms "$V_H$" and "high volume" are used interchangeably here and shall mean that after an aerosolized dose is created the patient inhales the dose and continues to inhale a high volume. More specifically, the patient inhales a high volume which is approximately 80% or more of the patient's total lung capacity. For an adult with a 5 liter lung volume the inhalation would be approximately 4 liters or more i.e. up to the total lung volume. Some error should be accounted for. Thus the high volume can be 65% to 100% of the total lung volume depending on the lung volume of the patient. Within the specific examples shown here the high inhaled volume for healthy male patients with a total lung volume of approximately 5 liters was in general about 4.7 liters. High volume is preferably as close to 100% as the patient can inhale.

The terms "$V_L$" and "Low volume" refer to a smaller inhaled volume as compared to an inhaled high volume of air with the aerosolized delivery of insulin. Even without inhaling the lung will retain some air. Thus, a low inhaled volume is approximately 40% plus or minus 15% of the patient's total lung volume. For the experiments shown here a low inhaled volume involved inhaling approximately 3 liters or less. It should be noted that inhaled volumes are volumes recorded at Body Temperature and Pressure Standard, i.e. the units are liters (btps). The terms $V_L$ $V_H$ can be further understood in connection with FIG. 3 and it description.

The term "acceptable serum glucose level" is intended to mean a glucose level above 50 mg/dl and below 300 mg/dl, more preferably 80 mg/dl to 200 mg/dl and most preferably about 100 mg/dl. It will be understood by those skilled in the art that levels of about 50 mg/dl are considered low and that levels of about 300 mg/dl are considered high, although acceptable in the sense that these levels are generally not fatal. It is an important aspect of the invention to maintain more acceptable levels which are above the low of 50 mg/dl and below the high of 300 mg/dl with it being more acceptable to deliver doses of insulin so as to keep the patient as close as possible to about 100 mg/dl.

The term "blood concentration versus time profile" shall be interpreted to mean the concentration of a drug in the blood or plasma over time. This can be characterized by means of a graph showing the concentration of a drug (e.g. insulin or an insulin analog or "immunoreactive insulin" as a surrogate measurement for an insulin analog such as insulin lispro) on the Y axis and time on the X axis. The blood concentration versus time profile can also be characterized by certain pharmacokinetic parameters such as $C_{max}$ (the maximum concentration of the drug seen over the measured time interval) and $T_{max.}$ (the time at which $C_{max}$ was observed). Note that, by these criteria, two different blood concentration versus time profiles may be associated with similar or even identical bioavailability measurements. The blood concentration versus time profile is crucial for drugs such as insulin and insulin analogs where the time at which peak concentration preferably occurs in relation to the using blood glucose levels following a meal. Different values of $T_{max}$ for two different insulin preparations or delivery methods could therefore be associated with significant differences in safety and efficacy.

The term "dosing event" shall be interpreted to mean the administration of regular insulin and/or monomeric insulin to a patient in need thereof by the intrapulmonary route of administration which event may encompass one or more releases of formulation from a dispensing device (from one or more containers) over a period of time of 15 minutes or less, preferably 10 minutes or less, and more preferably 5 minutes or less, during which period one or more inhalations are made by the patient and one or more doses of regular insulin or monomeric insulin are released and inhaled. A dosing event shall involve the administration of regular insulin or monomeric insulin to the patient in an amount of about 1 unit to about 30 units in a single dosing event which may involve the release of from about 1 to about 300 units from the device.

The term "inspiratory flow rate" shall mean a value of air flow rate measured, calculated and/or determined based on the speed of the air passing a given point in a measuring device assuming atmospheric pressure 5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, 5% and temperature in the range of about 10° C. to about 40° C.

The term "inspiratory volume" shall mean a determined, calculated and/or measured volume of air passing a given point into the lungs of a patient assuming atmospheric pressure ±5% and a temperature in the range of 10° C. to 40° C.

The term "inhaling maximally" shall mean that the patient makes a maximal effort to inhale air into the lungs.

The term "inspiratory flow profile" shall be interpreted to mean data calculated in one or more events measuring inspiratory flow and cumulative volume, which profile can be used to determine a point within a patient's inspiratory cycle which is preferred for the release of aerosol to be delivered to a patient. The point within the inspiratory cycle where drug is released may be based on a point within the inspiratory cycle likely to result in the maximum delivery of drug and/or based on a point in the cycle most likely to result in the delivery of a reproducible amount of drug to the patient at each release of drug. Repeatability of the amount delivered is the primary criterion and maximizing the amount delivered is an important but secondary criterion. Thus, a large number of different drug release points might be selected and provide for repeatability in dosing provided the selected point is again selected for subsequent releases. To insure maximum drug delivery the point is selected within given parameters.

The term "therapeutic index" refers to the therapeutic index of a drug defined as the ratio of toxic to therapeutic dose. Drugs with a therapeutic index near unity achieve their therapeutic effect at doses very close to the toxic level and as such have a narrow therapeutic window, i.e. a narrow dose range over which they may be administered.

The term "liquid formulation" is used herein to describe any pharmaceutically active insulin, including insulin and/or monomeric insulin for treating diabetes mellitus by itself or with a pharmaceutically acceptable carrier in flowable liquid form and preferably having a viscosity and other characteristics such that the formulation is aerosolized into particles which are inhaled into the lungs of a patient after the formulation is moved through a porous membrane of the invention. Such formulations are preferably solutions, e.g. aqueous solutions, ethanolic solutions, aqueous/ethanolic solutions, saline solutions and colloidal suspensions. Formulations can be solutions or suspensions of drug in any fluid including fluids in the form of a low boiling point propellant.

The term "formulation" is used to encompass the term "liquid formulation" and to further include dry powders of insulin and/or monomeric insulin along with excipient materials. Preferred formulations are aqueous solutions of monomeric insulin but include dry powders and dispersions.

The term "substantially" dry shall mean particles of an aerosol which contain less than 10% free water, ethanol or other liquid carrier based on total weight and preferably contains no detectable free liquid carrier.

The term "bulk flow rate" shall mean the average velocity at which air moves through a channel considering that the flow rate is at a maximum in the center of the channel and at a minimum at the inner surface of the channel.

The term "flow boundary layer" shall mean a set of points defining a layer above the inner surface of a channel through which air flows wherein the air flow rate below the boundary layer is substantially below the bulk flow rate, e.g., 50% or less than the bulk flow rate.

The term "carrier" shall mean a non-active portion of a formulation. In aqueous formulations, it is a liquid, flowable, pharmaceutically acceptable excipient material which insulin and/or monomeric insulin is suspended in or more preferably dissolved in. In a dry powder, it shall include non-active components, e.g., to keep the particles separate. Useful carriers do not adversely interact with the monomeric insulin and have properties which allow for the formation of aerosolized particles—preferably particles having a diameter in the range of 0.5 to 3.0 microns when a formulation comprising the carrier and insulin analog is forced through pores having a diameter of 0.25 to 3.0 microns. Preferred carriers for liquid solutions include water, ethanol and mixtures thereof. Other carriers can be used provided that they can be formulated to create a suitable aerosol and do not adversely effect insulin, monomeric insulin or human lung tissue.

The term "measuring" describes an event whereby either the inspiratory flow rate or inspiratory volume of the patient is measured (via electronic sensors or by mechanical means) in order to determine an optimal point in the inspiratory cycle at which to release aerosolized drug. An actual measurement of both rate and volume may be made or the rate can be directly measured and the volume calculated based on the measured rate. It is also preferable to continue measuring inspiratory flow during and after any drug delivery and to record inspiratory flow rate and volume before, during and after the release of drug. Such reading makes it possible to determine if drug was properly delivered to the patient.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age.

General Methodology

The invention comprises aerosolizing a formulation of monomeric insulin (e.g. insulin lispro) and inhaling the aerosolized formulation into the lungs. Although the inhalation of insulin which results in the insulin entering the circulatory system is known, correctly dosing the amount of insulin delivered by inhalation has been problematic—however, see U.S. Pat. No. 5, 672,581 issued Sep. 30, 1997. The devices, formulations and methods disclosed herein are useful in solving problems with prior methods. For example, when regular insulin is delivered to a patient by inhalation the amount of effect on glucose levels varies considerably based on the lung volume inhaled by the patient with the aerosolized insulin at delivery. If the blood glucose level is not quickly lowered the patient may administer additional insulin which in combination with that already administered will dangerously lower the blood glucose level. The present invention endeavors to provide a preferred blood concentration versus time profile by the delivery of monomeric insulin which rapidly disassociates into its monomeric form in a human and as such moves into the circulatory system more rapidly as compared to regular insulin. When regular insulin is delivered by inhalation, the effect on lowering glucose levels is often different depending on the total inhaled volume of by the patient at delivery. Results provided here show that the delivery of monomeric insulin is much less effected by the patient's total inhaled volume at delivering as compared to the aerosolized delivery of regular insulin thereby improving repeatability of dosing. Thus, the data shown here provide improved unexpected results with respect to a practical method of treating Diabetes Mellitus by aerosolized drug delivery.

Figure 2:
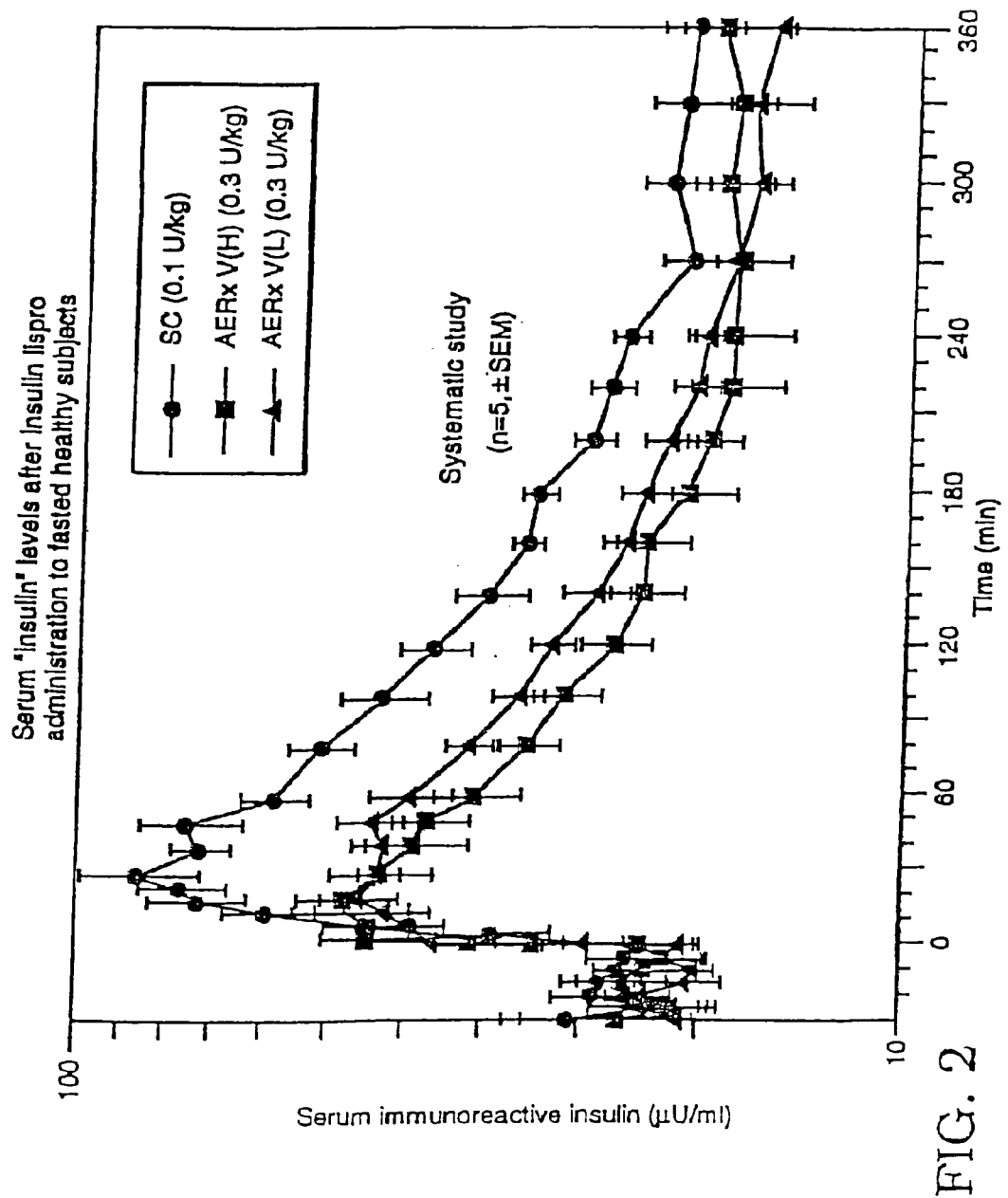
FIG. 2 is a graph plotting the change in immunoreactive insulin in blood serum over time following different methods of insulin lispro administration.

FIGS. 1 and 2 along with tables 1 and 2 dramatically show how the total inhaled volume at delivery has a dramatically greater effect on the blood concentration versus time profile following aerosolized delivery of insulin as compared to aerosolized delivery of monomeric insulin. In tables 1 and 2 as well as within FIGS. 1 and 2 a reference is made to "$V_L$" and "$V_H$" which refers to low volume and high volume inhalations at delivery respectively. A more complete understanding of what is meant by these terms and how the invention is carried out can be understood by reference to FIG. 3.

Figure 3:
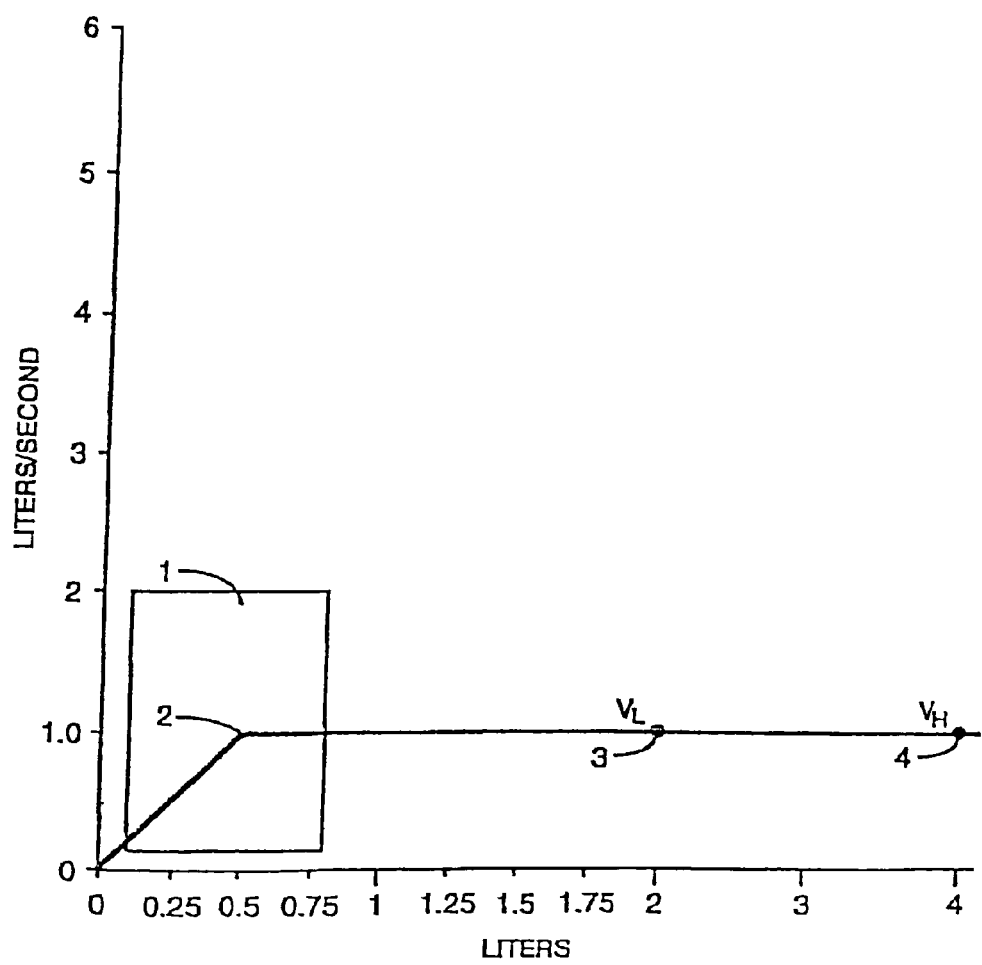
FIG. 3 is a graph showing $V_L$ and $V_H$ in a preferred breathing pattern at delivery.

FIG. 3 is a graph of inspiratory volume verses inspiratory flow rate in liters per second. Regardless of whether one is delivering insulin or monomeric insulin it is preferable to begin the release of the aerosolized dose to the patient when the inhaled inspiratory volume and inspiratory flow rate are within the parameters of the rectangle 1 shown in FIG. 3. In the specific example of FIG. 3 the release occurs at the point 2. The parameters of the rectangle shown indicate that release should occur at an inspiratory volume above 0.1 liter and prior to 0.8 liter. Further, the aerosol is released after the patients inhalation rate exceeds 0.1 liters per second but prior to the rate exceeding the 2.0 liters per second. In the examples shown the release occurs at an inspiratory volume of about 0.5 liters and at an inspiratory rate of about 1.0 liters per second. To enhance repeatability of dosing the patient would deliver each dose of insulin thereafter at the same inspiratory volume and inspiratory flow rate. More specifically the device of the invention will automatically release the aerosolized dose after it records an inspiratory volume of about 0.5 liters and an inspiratory flow rate of about 1 liter per second. Thereafter, the patient is coached to continue inhalation at the same rate e.g. at a rate of about 1 liter per second. For a low volume maneuver the inhalation is continued until the patient has inhaled 2 liters of air as shown by the point 3 in FIG. 3. For a high volume maneuver the patient continues inhaling until the patient has inhaled 4 liters of air or more as shown by point 4 in FIG. 3.

A comparison of FIGS. 1 and 2 as well as tables 1 and 2 shows that inhaling to a low or high volume at delivery does not effect the results significantly when delivery monomeric insulin—but substantially effects the results when delivering insulin The preferred monomeric insulin is insulin lispro as described in the 1997 PDR at page 1488 (incorporated herein by reference). This preferred monomeric insulin is also referred to herein by the commercial name "Humalog™." The following provides a description of the conceptual basis of the present invention.

Insulin has been used for over 50 years for the management of diabetes mellitus. Insulin is a naturally occurring hormone which plays a clinical role in glucose metabolism and its absence in patients with Type I Diabetes is a fatal illness unless exogenous insulin is used as part of an insulin replacement therapy program.

Patients have self administered insulin subcutaneously (SC) for decades as a means for managing their diabetes. The total daily dose of insulin required by individual patients varies. The availability of portable blood glucose monitors over the last decade has been a significant advancement in that patients can now measure their own blood glucose levels in self dose insulin by injection according to their needs. Many things affect the daily requirement for insulin. These multiple factors require that patients measure blood glucose levels to achieve tight control of their blood glucose.

The Diabetes Complications and Control Trial (DCCT), a multicenter study designed to evaluate the potential long term beneficial effects of tight blood glucose control, was recently completed. This study demonstrated that insulin requiring diabetics who maintained their serum glucose within a specific range over time had a significantly reduced complication rate, including the avoidance of the consequences of peripheral vascular disease (e.g. renal failure, chronic diabetic retinopathy and lower extremity problems).

A key element in the attainment of a stable blood glucose level over time involves the administration of subcutaneously administered insulin prior to meal time. In this way, blood levels of insulin will appear coincident with the increase in blood glucose associated with meal digestion. Recombinant human insulin, which has been available for over more than 10 years, is available in a short acting form (regular insulin) which is appropriate for self administration by injection prior to meal time. Unfortunately, recombinant human insulin must be dosed by injection approximately one half hour prior to meal time in order to insure that a rise in blood glucose does not occur unopposed by exogenous insulin levels.

The requirement that recombinant human insulin be injected one half hour prior to meal time is burdensome because it requires that patients precisely anticipate the times they will be eating. Eli Lilly has recently introduced insulin lispro which is sold as Humalog™ (a recombinant human insulin analog), which is more rapidly absorbed than recombinant human insulin when injected subcutaneously. Because it works more quickly than recombinant human insulin, Humalog™ can be given just prior to meal time thereby reducing the burden on the patient to plan ahead prior to eating.

Recombinant human insulin in aqueous solution is in a hexameric configuration. In other words, six molecules of recombinant insulin are noncovalently associated in a hexameric complex when dissolved in water in the presence of zinc ions. Studies have demonstrated that hexameric insulin is not rapidly absorbed from the subcutaneous space. In order for recombinant human insulin to be absorbed into circulation, the hexameric form must first dissociate into dimer and/or a monomeric forms i.e., these forms are required before the material can transit into the blood stream. This requirement for recombinant human insulin to disassociate from hexameric to dimer or monomeric form prior to absorption is believed to be responsible for the 30 minutes required for a self administered dose of subcutaneous recombinant human insulin to produce a measurable therapeutic blood level.

Although Humalog™ exists in solution outside the body as a hexamer, it very rapidly disassociates into a monomeric form following subcutaneous administration. Clinical studies have demonstrated that Humalog™ is absorbed quantitatively faster than recombinant human insulin after subcutaneous administration.

To control glucose levels insulin is dosed in units. Because insulin is generally in the form of regular insulin and is generally administered subcutaneously the units of measurements used here are subcutaneous equivalents of regular insulin.

Because insulin must be administered frequently in order to allow patients to attain a tight degree of control over their serum glucose, the fact that all insulin products currently need to be delivered by injection is a hindrance to compliance. Results from a DCCT study demonstrate that insulin should ideally be administered 4-6 times each day in order for patients to be likely to achieve an adequate level of blood glucose control to obtain a reduction in complication rate associated with diabetes. A noninvasive method for the delivery of insulin could be beneficial in increasing patient compliance with frequent self administration of insulin throughout the day.

The noninvasive delivery of proteins and peptides has been an elusive goal of the drug delivery industry. Because proteins are rapidly disassociated in the GI tract, oral forms for the delivery of proteins as tablets or capsules have thus far seen limited success. Inhalational drug delivery has been demonstrated to be a viable option for the delivery of proteins and peptides such as insulin via the lung, see U.S. Pat. No. 5,364,838, issued Nov. 15, 1994 and U.S. Pat. No. 5,672,581 issued Sep. 30, 1997.

Recent studies have demonstrated that insulin can be reproducibly administered for inhalation to healthy volunteers producing a rapid rise in measurable serum glucose level as well as a rapid fall in blood glucose. U.S. Pat. No. 5,544,646 describes systems for the intrapulmonary delivery of aerosolized aqueous formulations. The system described allows unit dosed packages of aqueous formulated drug to be delivered deep into the lung for systemic effect. U.S. Pat. No. 5,558,085, Intrapulmonary Delivery of Peptide Drugs illustrates how proteins and peptides can be delivered as fine particle aerosols through the lung for systemic effect. U.S. Pat. No. 5,497,763 describes a disposable package for intrapulmonary delivery of aerosolized formulations which allows sealed packets of preformulated drugs such as insulin to be inserted by the patient into aerosolization apparatus for producing fine particle aerosols for deep inhalation.

By quantitatively measuring the inspiratory flow rate and volume during the patients inspiratory maneuver while breathing through the aerosolization system, an optimum point for the delivery of a bolus of aerosolized medication can be determined. U.S. Pat. No. 5,509,404 describes intrapulmonary drug delivery within therapeutically relevant inspiratory flow volume values and illustrates how specific inspiratory flow rate and flow volume criteria can be used to enhance the reproducibility of drugs delivered via the lung for systemic effect. U.S. Pat. No. 5,522,385, Dynamic Particle Size Control for Aerosolized Drug Delivery demonstrates that the parameters of the emitted aerosol can be varied to optimize the delivery of an inhaled aerosol for systemic effect.

U.S. patent application Ser. No. 08/754,423, filed Nov. 11, 1996, illustrates that recombinant human insulin, when delivered as an aerosol for deep inhalation into the lung for systemic effect, is sequestered in the lung to a significant degree. This U.S. patent application describes how insulin sequestered within the lung can be made to transit into the systemic circulation if the patient engages in certain specific inspiratory maneuvers following delivery.

Although the reasons for sequestration of insulin in the lung following aerosolized delivery are not known, we speculate that, as with subcutaneous delivery, the dissociation of insulin from hexameric to monomeric form is an important first step prior to the absorption of insulin into the blood stream. Recent controlled experiments conducted by the inventors quantified the degree to which insulin is sequestered into the lung following aerosolized delivery. In these controlled experiments, the amount of insulin or monomeric insulin released into the blood stream following aerosol delivery was quantified in cross over fashion with and then without a forced expiratory maneuver following delivery. Results shown here indicated that the blood concentration versus time profile of monomeric insulin is not substantially affected compared to insulin by a patient's respiratory maneuver at delivery.

Although multiple studies have evaluated the feasibility of the delivery of recombinant human insulin via the lung as a fine particle aerosol, no studies have appeared demonstrating that recombinant human insulin is sequestered in the lung following aerosolized delivery. Recently conducted clinical studies demonstrate that significant sequestration of recombinant human insulin is occurring in the lung following aerosol drug delivery. Although this degree of sequestration can be reversed by certain specific pulmonary maneuvers as shown in our copending application, it will be desirable to substantially reduce or eliminate this sequestration altogether.

Because Humalog™ rapidly disassociates into monomeric insulin, it is uniquely suited for delivery via the lung.

The invention includes containers, devices and methods which provide a non-invasive means of treating diabetes mellitus in a manner which makes it possible to accurately dose the administration of aerosolized monomeric insulin and thereby maintain tight control over serum glucose levels of a patient suffering from the disease. The device of the invention provides a number of features which make it possible to achieve the controlled and repeatable dosing procedure required for treating diabetes.

Specifically, the device is not directly actuated by the patient in the sense that no button is pushed nor valve released by the patient applying physical pressure. On the contrary, the device of the invention provides that aerosolized insulin formulation is released automatically upon receipt of a signal from a microprocessor programmed to send a signal when data is received from a monitoring device such as an airflow rate monitoring device.

A patient using the device withdraws air from a mouthpiece and the inspiratory rate of the patient is measured as is cumulative inspiratory volume. The monitoring device continually sends information to the microprocessor, and when the microprocessor determines that the optimal point in the respiratory cycle is reached, the microprocessor actuates the opening of the valve allowing release of insulin. Accordingly, drug is always delivered at a pre-programmed place in the respiratory flow profile of the particular patient which is selected specifically to maximize reproducibility of drug delivery to the peripheral lung regions. It is pointed out that the device of the present invention can be used to, and actually does, improve the efficiency of drug delivery. However, this is not a critical feature. Important features are the enhanced repeatability of blood concentration versus time profile and the increased rate at which insulin is brought into the circulatory system. The invention makes it possible to deliver a tightly controlled amount of drug at a particular point in the inspiratory cycle so as to assure the delivery of a controlled and repeatable amount of drug to the lungs of each individual patient.

The automatic control of monomeric insulin release provides a repeatable means controlling the glucose level of a patient. Because aerosolized monomeric insulin formulation is released automatically and not manually, it can predictably and repeatedly be released in the same amount each time to provide a preprogrammed measured amount which is desired.

When it is desirable to decrease particle size by heating, a heating element is used. The amount of heat added to the air is about 20 Joules or more, preferably 20 Joules to about 100 Joules and more preferably 20 Joules to about 50 Joules per 10 μl of formulation.

There is considerable variability with respect to the amount of insulin which is delivered to a patient when the insulin is being administered by injection. Patients requiring the administration of injectable insulin use commercial insulin which is prepared in concentrations of 100 units per milliliter, although higher concentrations up to about 1,000 units per milliliter can be obtained. It is preferable to use more highly concentrated monomeric insulin in connection with the present invention. If insulin containing 500 units of insulin per milliliter is used and a patient is administering 25 units, then the patient will only need to administer 0.05 milliliters of the concentrated insulin to the lungs of the patient to achieve the desired dose.

The symptoms of diabetes can be readily controlled with the administration of insulin. However, it is extremely difficult, to normalize the blood sugar throughout a 24-hour period utilizing traditional insulin therapy given as one or two injections per day. It is possible to more closely approach normalized blood sugar levels with the present invention. Improvements are obtained by smaller, more frequent dosing and by timing dosing relative to meals, exercise and sleep.

The precise amount of insulin administered to a patient varies considerably depending upon the degree of the disease and the size of the patient. A normal-weight adult may be started on about a 15-20 units a day (as explained above the units are equivalent subcutaneous units) in that the estimated daily insulin production rate in non-diabetic subjects of normal size is approximately 25 units per day. It is preferable to administer approximately the same quantity of insulin for several days before changing the dosing regime except with hypoglycemic patients for which the dose should be immediately decreased unless a clearly evident nonrecurrent cause of hypoglycemia (such as not eating, i.e., missing a typical meal) is present. In general, the changes should not be more than five to ten units per day. It is typical to administer about two-thirds of the total insulin daily dosage before breakfast and administer the remainder before supper. When the total dosage reaches 50 or 60 units per day, a plurality of smaller doses are often required since peak action of insulin appears to be dose related, i.e., a low dose may exhibit maximal activity earlier and disappear sooner than a large dose. All patients are generally instructed to reduce insulin dosage by about 5 to 10 units per day when extra activity is anticipated. In a similar manner, a small amount of extra insulin may be taken before a meal that contains extra calories or food which is not generally eaten by the diabetic patient. The inhalation device of the present invention is particularly useful with respect to providing such small amounts of additional insulin.

Several types of insulin formulations are commercially available. When larger doses of insulin must be administered at a single point in time, it may be preferable to administer intermediate or long-acting insulin formulations. Such formulations release some insulin immediately and provide a more sustained release of the remainder of the insulin over time. Such formulations are described further below in the "Insulin Containing Formulations" section.

There is a differential between the amount of insulin and/or monomeric insulin actually released from the device and the amount actually delivered to the patient. The present device is two to ten times more efficient than conventional inhalation devices (i.e., MDIs or metered dose inhalers) which have an efficiency as low as 10% meaning that as little as 10%. of the aerosolized insulin may actually reach the lungs of the patient. The efficiency of the delivery will vary somewhat from patient to patient and should be taken into account when programming the device for the release of insulin.

One of the difficulties with aerosolized delivery of insulin is that the patient and/or the caregiver cannot determine precisely how much insulin has entered the circulatory system. Accordingly, if the patient has been dosed with what is believed to be an adequate amount of aerosolized insulin and the glucose level remains high one might assume that the aerosolized dose was not properly delivered. For example, the insulin might have been improperly delivered against the patient's mouth surfaces or throat where it will not be absorbed into the circulatory system. However, it may be that the insulin is properly delivered to the lung (e.g., provided on the outer peripheral areas of the lung) but has not yet migrated into the circulatory system.

Obese patients are generally somewhat less sensitive to insulin and must be provided with higher doses of insulin in order to achieve the same effect as normal weight patients. Dosing characteristics based on insulin sensitivity are known to those skilled in the art and are taken into consideration with respect to the administration of injectable insulin. The present invention makes it possible to vary dosing over time if insulin sensitivity changes and/or if user compliance and/or lung efficiency changes over time.

Based on the above, it will be understood that the dosing or amount of monomeric insulin actually released from the device can be changed based on the most immediately prior monitoring event wherein the inspiratory flow of a patient's inhalation is measured. The amount of insulin released can also be varied based on factors such as timing and timing is, in general, connected to meal times, sleep times and, to a certain extent, exercise times. Although all or any of these events can be used to change the amount of insulin released from the device and thus the amount of insulin delivered to the patient, ultimately, the amount released and delivered to the patient is based on the patient's serum glucose levels. It is important to maintain the serum glucose levels of the patient within acceptable levels (greater than 60 mg/dl and less than 125 mg/100 ml, and most preferably to maintain those levels at about 80 mg/100 ml.

Variations in doses are calculated by monitoring serum glucose levels in response to known amounts of insulin released from the device. If the response in decreasing serum glucose level is higher than with previous readings, then the dosage is decreased. If the response in decreasing serum glucose level is lower than with previous readings, then the dosing amount is increased. The increases and decreases are gradual and are preferably based on averages (of 10 or more readings of glucose levels after 10 or more dosing events) and not a single dosing event and monitoring event with respect to serum glucose levels. The present invention can record dosing events and serum glucose levels over time, calculate averages and deduce preferred changes in administration of insulin.

As another feature of the invention, the device can be programmed so as to prevent the administration of more than a given amount of insulin within a given period of time. For example, if the patient normally requires 25 units per day of insulin, the microprocessor of the inhalation device can be programmed to prevent further release of the valve after 35 units has been administered within a given day. Setting a slightly higher limit would allow for the patient to administer additional insulin, if needed, due to larger than normal meals and/or account for misdelivery of insulin such as due to coughing or sneezing during an attempted delivery.

The ability to prevent overdosing is a characteristic of the device due to the ability of the device to monitor the amount of insulin released and calculate the approximate amount of insulin delivered to the patient based on monitoring given events such as airflow rate and serum glucose levels. The ability of the present device to prevent overdosing is not merely a monitoring system which prevents further manual actuation of a button. As indicated above, the device used in connection with the present invention is not manually actuated, but is fired in response to an electrical signal received from a microprocessor. Applicant's device does not allow for the release of insulin merely by the manual actuation of a button to fire a burst of insulin into the air.

The microprocessor of applicant's invention can be designed so as to allow for an override feature which would allow for the administration of additional insulin. The override feature could be actuated in an emergency situation. Alternatively, the override feature could be actuated when the device is electronically connected with a serum glucose level monitoring device which determines that serum glucose levels increase to dangerously high levels.

The microprocessor of applicant's invention will preferably include a timing device. The timing device can be electrically connected with visual display signals as well as audio alarm signals. Using the timing device, the microprocessor can be programmed so as to allow for a visual or audio signal to be sent when the patient would be normally expected to administer insulin. In addition to indicating the time of administration (preferably by audio signal), the device can indicate the amount of insulin which should be administered by providing a visual display. For example, the audio alarm could sound alerting the patient that insulin should be administered. At the same time, the visual display could indicate "five units" as the amount of insulin to be administered. At this point, a monitoring event could take place. After the predetermined dose of five units had been administered, the visual display would indicate that the dosing event had ended. If the patient did not complete the dosing event by administering the stated amount of insulin, the patient would be reminded of such by the initiation of another audio signal, followed by a visual display instructing the patient to continue administration.

Additional information regarding dosing with insulin via injection can be found within Harrison's C Principles of Internal Medicine (most recent edition) published by McGraw Hill Book Company, New York, incorporated herein by reference to disclose conventional information regarding dosing insulin via injection.

Treatment Via Monomeric Insulin

The methodologies of the present invention are preferably carried out using recombinantly produced monomeric insulin in a liquid formulation. A preferred insulin is insulin lispro, sold by Lilly under the name Humalog™. This analog is absorbed faster after subcutaneous injection. Another type of insulin analog is referred to as superactive insulin. In general, superactive insulin has increased activity over natural human insulin. Accordingly, such insulin can be administered in substantially smaller amounts while obtaining substantially the same effect with respect to reducing serum glucose levels. Another general type of analog is referred to as hepatospecific insulin. Hepatospecific insulin analogs are more active in the liver than in adipose tissue and offer several advantages over currently available insulin therapy. Hepatospecific analogs provide preferential hepatic uptake during peripheral subcutaneous administration, thereby mimicking, more closely, the metabolic balance between the liver and the peripheral tissues. Obtaining the correct metabolic balance is an important part of proper treatment of diabetics and administration via the intrapulmonary route should provide advantages over intermuscular injection with respect to obtaining such a balance. It may be desirable to include mixtures of conventional insulin with insulin lispro or with insulin which is hepatospecific and/or with superactive insulin analogs. Hepatospecific analogs are disclosed and described within published PCT application WO90/12814, published Nov. 1, 1990, which application is incorporated herein by reference for its disclosure of such hepatospecific insulin analogs and in order to disclose other information cited within the other publications referred to within WO90/12814. To carry out the invention these insulins must be in a monomeric form or take a monomeric form quickly in a human.

U.S. patent application Ser. No. 074,558 discloses a superactive human insulin analog, [10-Aspartic Acid-B] human insulin, which has increased activity over natural human insulin. Specifically, [10-Aspartic Acid-B] human insulin was determined to be 4 to 5 times more potent than natural insulins. U.S. patent application Ser. No. 273,957 and International application Ser. No. PCT/US88/02289 disclose other superactive insulin analogs, des-pentapeptide (B26-B30)-[$Asp^{B10}$, $Tyr^{B25}$-α-carboxamide] human insulin, (B26-B30)-[$Glu^{B10}$, $Tyr^{B25}$-α-carboxamide] human insulin, and further insulin analogs of the formula des(B26-B30)-[$X^{B10}$, $Tyr^{B25}$-α-carboxamide] human insulin, in which X is a residue substituted at position 10 of the B chain. These insulin analogs have potencies anywhere from 11 to 20 times that of natural human insulin. All of the above-described insulin analogs involve amino acid substitutions along the A or B chains of natural human insulin, which increase the potency of the compound or change other properties of the compound.

Other than insulin lispro the insulin analogs are not presently used for the treatment of patients on a commercial scale. However, insulin lispro and other insulin analogs being developed could be used with the present invention in that the present invention can be used to provide variable dosing in response to currently measured serum glucose levels. Further, since many insulin analogs are more potent than conventional insulin, their delivery via the intrapulmonary route is particularly convenient.

Information regarding dosing insulin can be found within Harrison's -Principles of Internal Medicine (most recent edition) and the Drug Evaluation Manual, 1993 (AMA-Division of Drugs and Toxicology), both of which are published by McGraw Hill Book Company, New York, incorporated herein by reference to disclose conventional information regarding dosing of insulin.

Monitoring Diabetic Control

All methods of treating diabetes involve measuring glucose levels in some manner. Such measurements are necessary in order to titrate proper dosing and avoid the overadministration of insulin which can result in fatal hypoglycemia. Measurements of urine glucose alone are insufficient to assess diabetic control and bring mean plasma glucose values into a near normal range since the urine will be free of glucose when the plasma concentration is relatively normal. For this reason, "home glucose monitoring" is used in those patients treated by continuous subcutaneous insulin infusion (CSII) or multiple subcutaneous injection (MSI) techniques. Such monitoring requires capillary blood which can be obtained in a substantially painless manner using a small spring-triggered device referred to as Autolet™ produced by Ulstr Scientific Incorporated which device is equipped with small disposable lancelets. The amount of glucose is analyzed using chemically impregnated strips which are read in a commercially available reflectance meter. One commercially available strip is referred to as Chemstrip bG (produced by Bio-Dynamics). The Chemstrip Bg can provide satisfactory values by visual inspection utilizing a dual-color scale, thus eliminating the need for a reflectance meter. Frequent measurement of the plasma glucose (a fairly standard program utilizes seven or eight assays over a 24-hour period) allows a reasonable assessment of mean plasma glucose levels during the day and guides adjustment of insulin dosage.

The methodology of the present invention is preferably utilized in combination with a closely controlled means of monitoring serum glucose levels. More specifically, the invention is used to administer doses of monomeric insulin via the intrapulmonary route. The doses may be administered more frequently but in somewhat smaller amounts than are generally administered by injection. The amount of insulin and monomeric insulin administered can be readily adjusted in that smaller amounts are generally administered using the intrapulmonary delivery methodology of the present invention.

During the day, as insulin is administered, serum glucose levels are frequently monitored. The amount of insulin administered can be dosed based on the monitored serum glucose levels, i.e., as glucose levels increase, the amount of insulin can be increased, and as glucose levels are seen to decrease, the dosing of insulin can be decreased.

Based on the information disclosed herein in combination with what is known about insulin dosing and serum glucose levels, computer readable programs can be readily developed which can be used in connection with the insulin delivery device of the present invention. More specifically, a microprocessor of the type disclosed in U.S. Pat. No. 5,542,410 can be programmed so as to deliver precise doses of insulin which correspond to the particular needs of the patient based on serum glucose monitoring information which is supplied to the microprocessor. Further, the dosing information contained within the microprocessor can be fed to a separate computer and/or serum glucose monitoring device (preferably portable) in order to calculate the best treatment and dosing schedule for the particular patient.

Insulin Containing Formulations

A variety of different monomeric insulin containing formulations can be used in connection with the present invention. The active ingredient within such formulations is monomeric insulin which can be combined with regular insulin. Further, the monomeric insulin may be combined with an insulin analog which is an analog of human insulin which has been recombinantly produced. Although the monomeric insulin is generally present by itself as the sole active ingredient, it may be present with an additional active ingredient such as a sulfonylurea. However, such sulfonylureas are generally administered separately in order to more closely control dosing and serum glucose levels.

The present invention provides a great deal of flexibility with respect to the types of monomeric insulin formulations to be administered. For example, a container can include monomeric insulin by itself or in combination with an analog of any type or combinations of different insulin analogs. Further, a package can be created wherein individual containers include different formulations wherein the formulations are designed to achieve a particular effect e.g., fast acting insulin or quick absorbing insulin. The patient along with the care giver and careful monitoring can determine the preferred insulin dosing protocol to be followed for the particular patient.

The monomeric insulin may be provided as a dry powder by itself, and in accordance with another formulation, the insulin or active ingredient is provided in a solution formulation. The dry powder could be directly inhaled by allowing inhalation only at the same measured inspiratory flow rate and inspiratory volume for each delivery. However, the powder is preferably dissolved in an aqueous solvent to create a solution which is moved through a porous membrane to create an aerosol for inhalation.

Any formulation which makes it possible to produce aerosolized forms of monomeric insulin which can be inhaled and delivered to a patient via the intrapulmonary route can be used in connection with the present invention. Specific information regarding formulations (which can be used in connection with aerosolized delivery devices) are described within Remington's Pharmaceutical Sciences, A. R. Gennaro editor (latest edition) Mack Publishing Company. Regarding insulin formulations, it is also useful to note Sciarra et al. [*Journal of Pharmaceutical Sciences,* Vol. 65, No. 4, 1976].

The monomeric insulin is preferably included in a solution such as the type of solution which is made commercially available for injection and/or other solutions which are more acceptable for intrapulmonary delivery. When preparing preferred formulations of the invention which provide for the monomeric insulin, excipient and solvent, any pharmaceutically acceptable excipient may be used provided it is not toxic in the respiratory tract. The monomeric insulin formulation preferably has a pH of about 7.4±1.0.

Formulations include monomeric insulin dry powder by itself and/or with an excipient. When such a formulation is used, it may be used in combination with a gas propellant which gas propellant is released over a predetermined amount of dried powder which is forced into the air and inhaled by the patient. It is also possible to design the device so that a predetermined amount of dry powder is placed behind a gate. The gate is opened in the same manner as the valve is released so that the same inspiratory flow rate and inspiratory volume is repeatedly obtained. Thereafter, the dry powder is inhaled by the patient and the insulin is delivered.

Rapidly acting preparations are always indicated in diabetic emergencies and in CSII and MSI programs. Intermediate preparations are used in conventional and MSI regimens. It is not possible to delineate precisely the biologic responses to the various preparations because peak effects and duration vary from patient to patient and depend not only on route of administration but on dose. The various insulins are available as rapid (regular, semilente), intermediate (NPH, lente, globin), and long-acing (PZI, ultralente) preparations, although not all manufacturers offer all varieties. Lente and NPH insulin are used in most conventional therapy and are roughly equivalent in biologic effects. These can be used with monomeric insulin.

The methodology of the invention may be carried out using a portable, hand-held, battery-powered device which uses a microprocessor component as disclosed in U.S. Pat. No.

5,404,871, issued Apr. 11, 1995 and U.S. Pat. No. 5,450,336, issued Sep. 12, 1995 both of which are incorporated herein by reference. In accordance with another system the methodology of the invention could be carried out using the device, dosage units and system disclosed in U.S. Ser. No. 94/05825 with modifications as described herein. Monomeric insulin is included in an aqueous formulation which is aerosolized by moving the formulation through a flexible porous membrane. Alternatively, the methodology of the invention could be carried out using a mechanical (non-electronic) device. Those skilled in the art recognized that various components can be mechanical set to actuate at a given inspiratory flow rate (e.g. a spring biased valve) and at a given volume (e.g. a spinable flywheel which rotates a given amount per a given volume). The components of such devices could be set to allow drug release inside defined parameters.

The monomeric insulin which is released to the patient may be in a variety of different forms. For example, the insulin may be an aqueous solution of drug, i.e., drug dissolved in water and formed into small particles to create an aerosol which is delivered to the patient. Alternatively, the drug may be in a solution or a suspension wherein a low-boiling point propellant is used as a carrier fluid. In yet, another embodiment the insulin may be in the form of a dry powder which is intermixed with an airflow in order to provide for delivery of drug to the patient. Regardless of the type of drug or the form of the drug formulation, it is preferable to create drug particles having a size in the range of about 0.5 to 12 microns, more preferably 1-4 microns. By creating drug particles which have a relatively narrow range of size, it is possible to further increase the efficiency of the drug delivery system and improve the repeatability of the dosing. Thus, it is preferable that the particles not only have a size in the range of 0.5 to 12 microns but that the mean particle size be within a narrow range so that 80% or more of the particles being delivered to a patient have a particle diameter which is within 20% of the average particle size, preferably 10% and more preferably 5% of the average particle size.

An aerosol may be created by forcing drug through pores of a membrane which pores have a size in the range of about 0.25 to 6 microns preferably 0.5 to 3.0 microns. When the pores have this size the particles in the aerosol will have a diameter about twice the diameter of the pore opening from which the formulation exits. However, the particle size can be substantially reduced by adding heat to the air around the particles and cause evaporation of carrier. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency and amplitude, pressure, and other parameters based on the concentration, density, viscosity and surface tension of the formulation keeping in mind that the object is to provide aerosolized particles having a diameter in the range of about 0.25 to 12 microns, preferably 1.0-3.0 microns.

The drug formulation may be a low viscosity liquid formulation. The viscosity of the drug by itself or in combination with a carrier is not of particular importance except to note that the formulation preferably has characteristics such that it can be forced out of openings of the flexible or convex membrane to form an aerosol, e.g., using 20 to 400 psi to form an aerosol preferably having a particle size in the range of about 0.5 to 6.0 microns.

Drug may be stored in and/or released from a container of any desired size. In most cases the size of the container is not directly related to the amount of drug being delivered in that most formulations include relatively large amounts of excipient material e.g. water or a saline solution. Accordingly, a given size container could include a wide range of different doses by varying drug concentration.

Drug containers may include indices which may be electronic and may be connected to a power source such as a battery. When the indices are in the form of visually perceivable numbers, letters or any type of symbol capable of conveying information to the patient. Alternatively, the indices may be connected to a power source such as a battery when the indices are in the form of magnetically, optically or electronically recorded information which can be read by a drug dispensing device which in turn provides visual or audio information to the user. The indices can be designed for any desired purpose but in general provide specific information relating to the day and/or time when the drug within a container should be administered to the patient. Such indices may record, store and transfer information to a drug dispensing device regarding the number of doses remaining in the container. The containers may include labeling which can be in any format and could include days of the month or other symbols or numbers in any variation or language.

In addition to disclosing specific information regarding the day and time for drug delivery the indices could provide more detailed information such as the amount of insulin dispensed from each container which might be particularly useful if the containers included different amounts of insulin. The device may dispense all or any desired percentage amount (1-100%) of the insulin in the container. The device keeps a record of the amount dispensed and the container can be reused within a given period of time (e.g., 2 hours or less) to dispense the remainder of the insulin in a given container. However, it is preferable to discard a container after use even if all the formulation is not expelled. This ensures freshness and reduces contamination. Further, magnetic, optical and/or electronic indices could have new information recorded onto them which information could be placed there by the drug dispensing device. For example, a magnetic recording means could receive information from the drug dispensing device indicating the precise time (and amount) which the insulin was actually administered to the patient. In addition to recording the time of delivery the device could monitor the expected efficacy of the delivery based on factors such as the inspiratory flow rate which occurred following the initial release of insulin. The information recorded could then be read by a separate device, interpreted by the care-giver and used to determine the usefulness of the present treatment methodology. For example, if the glucose levels of the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicated that the patient had delivered the aerosolized insulin using the proper techniques and still not obtained the correct results (e.g. acceptable glucose levels) another dosing methodology might be recommended. The method of treating diabetes mellitus may be carried out using a hand-held, portable device comprised of (a) a device for holding a disposable package comprised of at least one but preferably a number of drug containers, (b) a propellant or a mechanical mechanism for moving the contents of a container through a porous membrane (c) a monitor for analyzing the inspiratory flow rate and volume of a patient, and (d) a switch for automatically releasing or firing the mechanical means after the inspiratory flow and/or volume reaches a threshold level. The device may also include a transport mechanism to move the package from one container to the next with each container and its porous membrane being disposed of after use. Containers are preferably used only 1,2,3 or 4 times, at most. If used more than once, the remainder in the container is used in 2 hours or less and/or disposed of. The entire device is self-contained, light weight (less than 1 kg preferably less than 0.5 kg loaded) and portable.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means (and/or a vibration device below the resonance cavity). When the actuation means is signaled, it causes the mechanical means (by pressure and/or vibration) to move drug from a container on the package into the inspiratory flow path of the device and ultimately into the patient's lungs. After being released, the drug and carrier will pass through a porous membrane, which can be vibrated to aerosolize the formulation and thereafter enter the lungs of the patient.

It is important to note that the firing threshold of the device is not based on a single criterion such as the rate of air flow through the device or a specific time after the patient begins inhalation. The firing threshold is preferably based on repeating the firing at the same flow rate and volume. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of (1) reproducibly delivering the same amount of drug to the patient with each release of drug by releasing drug at the same point each time and (2) maximizing the amount of drug delivered as a percentage of the total amount of drug released by releasing with the parameters described herein.

The device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means associated with disposable package.

The details of a drug delivery device which includes a microprocessor and pressure transducer of the type which may be used in connection with the present invention are described and disclosed within U.S. Pat. No. 5,404,871, issued Apr. 11, 1995 and U.S. Pat. No. 5,450,336, issued Sep. 12, 1995 incorporated in their entirety herein by reference, and specifically incorporated in order to describe and disclose the microprocessor and program technology used therewith. The pre-programmed information is contained within a non-volatile memory which can be modified via an external device. In another embodiment, this pre-programmed information is contained within a "read only" memory which can be unplugged from the device and replaced with another memory unit containing different programming information. In yet another embodiment, a microprocessor, containing read only memory which in turn contains the pre-programmed information, is plugged into the device. For each of these embodiments, changing the programming of the memory device readable by a microprocessor will radically change the behavior of the device by causing the microprocessor to be programmed in a different manner. This is done to accommodate different insulin formulation and for different types of treatment, e.g., patients with different types of diabetes.

After dosing a patient with insulin it is desirable to measure glucose (invasively or non-invasively) and make adjustments as needed to obtain the desired glucose level. In accordance with all methods the patient does not push a button to release drug. The drug is released automatically by signals from the microprocessor using measurements obtained.

The doses administered are based on an assumption that when intrapulmonary delivery methodology is used the efficiency of the delivery is at a known percent amount, e.g., approximately 20% to 50% or more and adjustments in the amount released in order to take into account the efficiency of the device. The differential between the amount of insulin actually released from any device and the amount actually delivered to the patient varies due to a number of factors. In general, devices used with the present invention can have an efficiency as low as 10% and as high as 50% or more meaning that as little as 10% of the released insulin may actually reach the circulatory system of the patient and as much as 50% or more might be delivered. The efficiency of the delivery will vary somewhat from patient to patient and must be taken into account when programming the device for the release of insulin. In general, a conventional metered (propellant-driven) dose inhaling device is about 10% efficient.

One of the features and advantages of the present invention is that the microprocessor can be programmed to take a variety of different criteria into consideration with respect to dosing times. Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of insulin within a given time. For example, the device could be programmed to prevent dispersing more than 5 units of insulin within one hour. More importantly, the device can be programmed to take both criteria into consideration. Thus, the device can be programmed to include a minimum time interval between doses and a maximum amount of insulin to be released within a given time period. For example, the microprocessor could be programmed to allow the release of a maximum of 5 units of insulin during an hour which could only be released in amounts of 1 unit with each release being separated by a minimum of five minutes.

Additional information regarding dosing with insulin via injection can be found within Harrison's C Principles of Internal Medicine (most recent edition) published by McGraw Hill Book Company, New York, incorporated herein by reference to disclose conventional information regarding dosing insulin via injection.

Another feature of the device is that it may be programmed not to release drug if it does not receive a signal transmitted to it by a transmitter worn by the intended user. Such a system improves the security of the device and prevents misuse by unauthorized users such as children.

The microprocessor of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices such as a glucose monitoring device. All of the features of the invention are provided in a portable, programmable, battery-powered, hand-held device for patient use which has a size which compares favorably with existing metered dose inhaler devices.

Different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation or other source of energy such as from compressed gas or a mechanical device would then cause the dry powder to form a dry dust cloud and be inhaled.

In addition to monitoring glucose levels in order to determine proper insulin dosing, the microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the valve when the inhalation cycle is repeated during the dosing event. Those skilled in the art will also readily recognize that different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation would then cause the dry powder to form a dry dust cloud and be inhaled. Dry powder can also be aerosolized by compressed gas, and a solution can be aerosolized by a compressed gas released in a similar manner and then inhaled.

EXAMPLES

The following examples are put forth so as to provide those of ordinary skill in the art with a complete disclosure and description of how to make and use various constructs and perform the various methods of the present invention and are not intended to limit the scope of what the inventors regard as their invention. Efforts have been made to ensure accuracy with respect to numbers used (e.g. amounts, concentrations, particular components, etc.) but some deviations should be accounted for.

Example 1

Administration of Regular Recombinant Human Insulin

A study was performed to determine the influence of different inhalation maneuvers: deep ($V_H$) and shallower ($V_L$) inhalation. Deep inhalations required the patients to inhale as much as possible (e.g., 4-5 liters) and shallow inhalation were about half that (e.g. 2-2.5 liters) following the administration of aerosolized drug). The study was performed using five healthy, fasting male subjects. To each of the subjects, 250 U/ml of a 7.4 pH human zinc insulin formulation was administered using three methods: subcutaneous administration, deep inhalation administration, or shallow inhalation administration.

The study was performed using five healthy, fasting male subjects. 250 U/ml of a 3.5 pH human insulin formulation was administered to each of the subjects using three methods: subcutaneous administration, $V_H$ inhalation administration and $V_L$ administration. Subcutaneous administration of the insulin consisted of an injection of a predetermined dosage into the subcutaneous region of the abdominal area. Aerosol administration to each subject was performed using a unit-dosed, breath-actuated microprocessor controlled device (AERx™), such as the device disclosed in the present application (see U.S. Pat. No. 5,660,166 issued Aug. 26, 1997).

Serial serum blood samples were taken from each subject for the analysis of plasma glucose. The inhalation method resulted in a more rapid initial change, and experienced a plateau at approximately a −20% change in plasma glucose. The subcutaneous administration resulted in a slower response initially, achieving a later plateau at approximately a −25% change in glucose response.

The pharmacokinetic parameters—$C_{max}$, the maximum serum insulin concentration achieved in each subject, and $T_{max}$, the amount of time needed for subjects to reach $C_{max}$ after administration were determined for each subject, and (summarized in Table 1). The deep inhalation method showed a 10-fold decrease in $T_{max}$.

TABLE 1

Inhaled human insulin: effect of mode of administration

| Parameter (meanSD) | AERx-$V_H$ | AERx-$V_L$ |
|---|---|---|
| $T_{max}$ (min) | 5 ± 6 | 51 ± 18 |
| $C_{max}$ (□U/ml) | 26.7 ± 9.1 | 20.9 ± 8.1 |

Serum insulin profiles of each of the three modes of administration show similar peaks before tapering off over a three hour period (FIG. 1). The AERx device $V_H$ administration peaks much sooner and at a higher concentration than the other methods, peaking at approximately 26 µU/ml at about 20 minutes. The AERx device $V_L$ administration results in a slightly later and lower peak at one hour. Subcutaneous injection also results in a later peak.

The study conducted with the regular zinc insulin pH 7.4 showed the importance of the breathing technique in the administration of this particular insulin formulation, as controlled, deep breathing promoted rapid insulin absorption.

The results of experiment 1 demonstrate one aspect of the present invention. Specifically, the results show that it is important to control the inhaled volume when inhaling an aerosolized dose of regular insulin. Thus, one aspect of the invention involves measuring a patient's inhaled volume at delivery in order to (1) repeatedly deliver with the same inhaled volume each time to ensure repeatability of dosing; and (2) prompt the patient to inhale a high volume, e.g. 80% plus or minus 15% of lung capacity with each inhalation. The prompting to inhale a high volume can be carried out by sending a signal to the patient from a device which measures the inspiratory volume during drug delivery.

Example 2

Determination of Efficacy of Administration of Aerosolized Human Insulin Lispro

Modes of administration

Pharmacokinetic parameters associated with the two modes of insulin administration, inhalation of aerosolized insulin lispro and subcutaneous injection of insulin lispro, were determined to compare the efficacy (bioeffectiveness in reducing glucose levels) and speed of each. The study was performed using nine healthy, fasted male subjects.

Aerosol administration to each subject was performed using the AERx™ device. Administration was done using both deep ($V_H$) and shallower ($V_L$) inhaled administration—in 5 out of 9 subjects. Subcutaneous administration of the insulin lispro consisted of an injection of a predetermined dosage into the subcutaneous region of the abdominal area. Serial serum blood samples were taken from each subject for the analysis of plasma glucose and serum insulin.

The pharmacokinetic parameters $C_{max}$ and $T_{max}$ were determined for each subject. (Table 2). $T_{max}$ was earlier following inhalation administration of insulin lispro, indicating a more rapid absorption from the lung as compared to SC administration. Thus, the mode of inhalation ($V_H$ or $V_L$) did not appear to significantly effect pharmacokinetics of the delivery of inhaled insulin lispro as compared to the affect of $V_L$ and $V_H$ on the delivering of regular insulin.

TABLE 2

Pharmacokinetic parameters after insulin lispro administration (systematic study, n = 5)

| Parameter (meanSD) | AERx-$V_H$ (0.3 U/kg) | AERx-$V_L$ (0.3 U/kg) |
|---|---|---|
| $T_{max}$ (min) | 9 ± 2 | 18 ± 15 |
| $C_{max}$ (μU/ml) | 46 ± 12 | 49 ± 12 |

In contrast to data obtained for aerosolized delivery of regular human insulin, the mode of inhalation did not lead to changes in the serum insulin levels following administration of insulin lispro—compare FIGS. 1 and 2.

The results in Tables 1 and 2 can be compared to show that the total inhaled volume at delivery greatly effects results when administering regular human recombinant insulin (Table 1) but has much less of an effect when administering insulin lispro. As shown in FIG. 2, the blood concentration versus time insulin lispro is virtually the same for both the $V_H$ and $V_L$ maneuvers. This surprising result indicates that repeatability of dosing can be more readily obtained with the administration of insulin lispro by inhalation as compared with conventional insulin by inhalation. The results shown here indicate that when delivering insulin (not monomeric insulin) by inhalation the total inhaled volume should be about the same at each delivery to obtain repeatable delivery. Thus, referring to FIG. 3, insulin is released at the same point 1 for each release and then the patient continues to inhale to the same point 3 or 4. Preferably, the patient continues to inhale to point 4 or higher each time to obtain repeatable delivery.

The foregoing invention has been described in some detail by way of illustration and example for purposes of clarity of understanding. The instant invention is shown herein in what is considered to be the most practical and preferred embodiments. It is recognized, however, that departures may be made therefrom which are within the scope of the invention and that obvious modifications will occur to one skilled in the art upon reading this disclosure. Accordingly, the invention is limited only by the following claims.

The invention claimed is:

1. A method, comprising the steps of:
   (a) measuring a patient's glucose level;
   (b) aerosolizing a formulation comprising monomeric insulin;
   (c) inhaling the aerosolized formulation into the lungs of the patient, the formulation being inhaled with a first total inhaled volume;
   (d) allowing particles of formulation to settle in the lungs, migrate into the patient's circulatory system and thereby increase the concentration to a first maximum level in the patient's blood in a first period of time;
   (e) repeating the aerosolizing of a formulation comprised of monomeric insulin;
   (f) inhaling the aerosolized formulation of (e) into the lungs of a patient, the formulation being inhaled with a second total inhaled volume different from the first total inhaled volume;
   (g) allowing particles of formulation to settle in the lungs, migrate into the patient's circulatory system and thereby increase the concentration of formulation to a second maximum level in the patient's blood in a second period of time;
   whereby the difference between the first total inhaled volume and the second total inhaled volume effects the difference between the first maximum level of formulation and the second maximum level of formulation less than if the formulation were comprised of regular recombinant insulin.

2. The method of claim 1, wherein the monomeric insulin is insulin lispro.

3. The method of claim 1, further comprising:
   repeating the (a) measuring, (b) aerosolizing, (c) inhaling and (d) allowing steps in a manner so as to maintain the patient's glucose level in a desired range.

4. The method of claim 3, wherein each aerosolizing (b) step is carried out to create an aerosolized dose containing substantially the same amount of monomeric insulin.

5. The method of claim 4, wherein the monomeric insulin is insulin lispro.

6. The method of claim 3, further comprising:
   orally administering a sulfonylurea drug to the patient.

7. The method of claim 6, wherein the sulfonylurea drug is chosen from acetohexamide, chlorpropamide, tolazamide, tolbutamide, glipzide and glyburide.

8. The method of claim 3, wherein the monomeric insulin is insulin lispro.

9. The method of claim 3, further comprising:
   heating air surrounding the aerosolized formulation.

10. The method of claim 3, wherein the aerosol comprises particles having a diameter in the range of about 1.0 to about 4.0 microns.

11. The method of claim 1, further comprising:
repeating the (b) aerosolizing; (c) inhaling and (e) allowing steps a plurality of times wherein the total inhaled volume is different in each of any different inhaling steps.

12. The method of claim 11, wherein the formulation is aerosolized by being forced through a porous membrane from a disposable container.

13. The method of claim 3, wherein the formulation is a liquid formulation comprised of a pharmaceutically acceptable carrier and insulin lispro and is present in a container comprising an opening covered by a porous membrane; and
wherein the aerosolizing (b) is carried out by moving the formulation through the pores of the membrane, the pores having a cross-sectional configuration with a small end opening of 0.25 to 6.0 microns in diameter and a large end opening of 2 to 20 times the diameter of the small end.

14. The method of claim 1, wherein the first total inhaled volume is about half the second total inhaled volume.

15. The method of claim 1, wherein the first total inhaled volume is in a range of about 2 to 2.5 liters and the second total inhaled volume is in a range of from about 4 to 5 liters.

16. A method of treating a diabetic patient, comprising:
(a) measuring a patient's glucose level;
(b) aerosolizing a formulation comprising monomeric insulin and a carrier to make an aerosol;
(c) inhaling a volume of the aerosol into a patient's lungs, thereby obtaining a maximum monomeric insulin concentration (CMAX) for the patient in a time needed to obtain a maximum concentration (TMAX) for the patient wherein said CMAX and TMAX are less affected by an amount of air inhaled during inhalation of or after aerosolizing the formulation as compared to an effect on CMAX and TMAX obtained with a formulation of regular hexameric recombinant insulin;
(d) measuring the patient's inspiratory flow rate and inspiratory volume; and
(e) repeatedly aerosolizing the formulation at the same measured inspiratory flow rate and inspiratory volume as measured in step (d); and
(f) maintaining serum glucose levels in the patient in a range of greater than 60 mg/dl and less than 125 mg/dl.

17. The method of claim 16, wherein the monomeric insulin is insulin lispro in a zinc salt form.

18. The method of claim 16, wherein the formulation is an aqueous solution.

19. The method of claim 16, wherein the formulation is a dry powder.

* * * * *